United States Patent [19]

Takahashi

[11] Patent Number: 4,957,864
[45] Date of Patent: Sep. 18, 1990

[54] NOVEL PLASMINOGEN ACTIVATOR AND ITS PREPARATION PROCESS

[75] Inventor: Seishi Takahashi, Yokohama, Japan

[73] Assignee: Mitsui Toatsu Chemicals, Incorporated, Tokyo, Japan

[21] Appl. No.: 213,489

[22] Filed: Jun. 30, 1988

Related U.S. Application Data

[63] Continuation of Ser. No. 66,524, Jun. 26, 1987, abandoned, which is a continuation of Ser. No. 621,918, Jun. 13, 1984, abandoned.

[30] Foreign Application Priority Data

Oct. 29, 1982 [JP] Japan ................................ 57-189067

[51] Int. Cl.$^5$ ............................................. C12N 9/64
[52] U.S. Cl. .................................... 435/226; 435/212; 435/219; 435/815; 424/94.64
[58] Field of Search ............... 435/212, 219, 226, 815; 424/94.64, 101, 103

[56] References Cited

U.S. PATENT DOCUMENTS

| | | | |
|---|---|---|---|
| 4,245,051 | 1/1981 | Reich | 435/212 |
| 4,317,823 | 3/1982 | Horiguchi | 435/215 |
| 4,381,346 | 4/1983 | Husain | 435/212 |

FOREIGN PATENT DOCUMENTS 0041766 12/1981 European Pat. Off. ............ 435/212

OTHER PUBLICATIONS

Sueishi, K. et al., Bioch. Biophys. Acta., 717:327-336, (1982).

Weimar, W. et al., The Lancet, Nov. 7, 1981, pp. 1018-1020.

Rijken, D. C. et al., J. Biol. Chem., 256(13):7035-7041, (7-1981).

Husain, S. S. et al., Proc. Natl. Acad. Sci., U.S.A., 78(7):4265-4269, (7-1981).

Aasted, B. et al., Biochim. Biophys. Acta., 621:241-254, (1980).

Binder, B. R. et al., J. Biol. Chem., 254(6):1998-2003, (1979).

Rijken, D. C. et al., (1979), Biochim. Biophys. Acta., 580, 140-153.

Rijken, D. C. et al., (1982), J. Biol. Chem., 257, 2920-2925.

Primary Examiner—Elizabeth C. Weimar
Assistant Examiner—Charles L. Patterson, Jr.
Attorney, Agent, or Firm—Fisher, Christen & Sabol

[57] ABSTRACT

A novel plasminogen activator having specific properties. The plasminogen activator can be prepared by subjecting a human kidney or human blood vessel to an extraction treatment with an ammonium thiocyanate solution and then allowing the resultant extract to pass through a column of ion exchanger, a metal chelate column, a column of L-arginine or an arginine derivative supported on a carrier, or a column of a carrier having properties as a molecular sieve to purify the same. The plasminogen activator exhibits a strong thrombolytic activity and is useful as an active ingredient of a thrombolytic composition accompanied with a minimum of side effects.

1 Claim, 5 Drawing Sheets

NOVEL PLASMINOGEN ACTIVATOR AND ITS PREPARATION PROCESS

This application is a continuation of application Ser. No. 066,524, filed June 26, 1987 now abandoned, which is a continuation of application 621,918, filed on June 13, 1984, now abandoned.

TECHNICAL FIELD

This invention relates to a novel plasminogen activator derived from a human tissue, for example, a human kidney or blood vessel and its preparation process.

BACKGROUND ART

Plasminogen activators may be classified, in accordance with their origins, into tissue activators, vascular activators, blood activators, urokinase, and the like. Plasminogen activators play an important role in fibrinolytic (fibrin-decomposing) activities and are found in a variety of organs of mammalian animals. On the other hand, a great deal of work has recently been made to obtain plasminogen activators from cultured cells. In the above work, there were used as cultured cells, for example, malignant tumor cells, blood vessel endothelium, stimulated macrophage, granular starch cells stimulated by follicle stimulating hormone, and the like. There have also been reported biochemical and immunological properties of plasminogen activators isolated from humoral tissue homogenates, cultured cells and culture media.

However, the purification of human tissue plasminogen activator has seldom been carried out. This is assumably attributed to difficulty in obtaining the starting material in a sufficient amount and, in addition, hydrophobic property of enzymes contained therein, low specific activity, instability of the enzymes in a buffer solution and, in some cases, presence of unknown protease in the course of the purification. Under these circumstances, Rijken et al.) "Biochimica et Biophysica Acta," vol. 580, pps. 140–153 (1979), isolated a human uterus plasminogen activator having a molecular weight of 69,000 and confirmed that the activator is similar both immunologically and biochemically to human vascular plasminogen activator. In addition, another human vascular plasminogen activator having a different molecular weight has also been isolated and identified.

Kwaan et al. [Fed. Proc. 24, 387 (1965)] carried out an investigation on a plasminogen activator derived from human kidney tissue and discovered that the activator is present principally in the endothelium of blood vessels, especially, in the endothelium of artery. It has also been reported by Kucinski et al. [J. Clin. Invest 47, 1238–1253 (1968)], Bernik et al. [J. Clin. Invest 48, 1740–1753 (1969)], Barlow et al. [Thromb. Res. 1, 201–208 (1972)]Åsted et al. [Experimentia 33, 589–590 (1978)] and Lewis {Thromb. Haemostas. 42, 895–890 (1970)] that such a plasminagen activator obtained from the cultivation of human kidney tissue is immunologically and physicochemically identical to urokinase.

As a result of an intensive investigation on the tissue plasminogen activator isolated and purified from human kidneys and human blood vessels, the present inventors have made a surprising finding of a plasminogen activator having properties significantly different from those of urokinase derived from human kidneys or human blood vessels, although it has been believed that urokinase is only the principal plasminogen activator available from human kidneys and human blood vessels. The present invention has been completed on the basis of this discovery.

DISCLOSURE OF THE INVENTION

It is an object of the present invention to provide a novel plasminogen activator.

It is a further object of the present invention to provide a process for preparing the novel plasminogen activator.

The novel plasminogen activator according to the present invention has the following characteristic properties:

(1) The main protein band obtained by sodium dodecyl sulfate-polyacrylamide gel electrophoresis has a molecular weight of approximately 70,000±5,000;

(2) The main band obtained by isoelectric-point electrophoresis has a pI in the range of 7 to 9;

(3) The plasminogen activator has the immunological property of not being adsorbed by anti-urokinase IgG-Sepharose affinity chromatography; and (4) The plasminogen activator hydrolyzes H-D-valyl-L-leucyl-L-lysine-p-nitroanilide ,dihydrochloride and H-D-isoleucyl-L-prolyl-L-arginine-p-nitroanilide dihydrochloride, but does not hydrolyze Boc-L-valyl-L-prolyl-L-arginine-4-methylcoumaryl-7-amide, carbobenzoxy-L phenylalanyl-L-arginine-4-methylcoumaryl-7-amide, L-prolyl L-phenylalanyl-L-arginine-4-methylcoumaryl-7-amide or glutaryl-glycyl-L-arginine 4-methylcoumaryl-7-amide.

The above plasminogen activator may preferably have the following additional properties:

(1) The plasminogen activator can be extracted or perfused from a tissue or blood vessel with a 1–2M NH4SCN solution (pH 7.4) and purified in the presence of a nonionic suface active agent such as 0.1% Tween 80 or the like;

(2) The plasminogen activator has the properties of being adsorbed practically completely onto a fibrin-Sepharose column and eluted with a 2M NH4SCN solution; and (3) The plasminogen activator remains unchanged after 2 weeks when stored at 4° C. in a buffer solution of pH 7.4.

The term "Stepharose" is a trademark and is a polymer obtained by cross-linking agarose with 2,3-dibromoppropanol. This is well-known in the art and described on page 328 of Biochimica et Biophysica Acta, 717 (1982) cited Sueishi et al.). DEAE-Sepharose has a

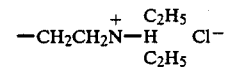

group bonded through —O— to agarose which is a constituent unit of Sepharose. Similarly, CM-Sepharose has a —CH2CO2− Na+ group.

The novel plasminogen activator of the present invention is prepared in such a manner that a human kidney is extracted with a buffer solution after removing blood clot, connective tissue, lipid and the like according to a method known per se in the art, or a human blood vessel is extracted by perfusion with an NH4SCN solution, and the resulting extract is purified by passing it through a column selected from the group consisting of a column of an ion exchanger, a metal chelate column, a column of L-arginine or an arginine derivative supported on a carrier, a column of a carrier having properties as a molecular sieve, and a column of hemagglutinin supported on a carrier or a combination of these columns to purify the same.

The novel plasminogen activator of the present invention provides an useful thrombolytic composition having strong thrombolytic effect capable of supplementing the immunological drawbacks of urokinase which is already available as a medicine having thrombolytic activity.

BEST MODE FOR CARRYING OUT THE INVENTION

The process according to the present invention and the properties of the novel plasminogen activator obtained by the process will be hereinafter described in detail. All the procedures were conducted at 4° C., unless otherwise specifically indicated.

EXAMPLE 1

Purification of plasminogen activator derived from kidney:

(1) Extraction of plasminogen activator:

A human kidney free of any infectious symptom (stored at $-70°$ C.) was added with acetone of $-15°$ C. and ground down in a homogenizer, after the mechanical removal of blood clot, connective tissue and lipids. The suspension was stirred at $-15°$ C. for 30 minutes and then allowed to stand at $-20°$ C. The surface flotage was removed by decantation and the defattening was repeated with acetone of $-15°$ C. The resultant suspension was then filtered. The filtered cake was washed with acetone of $-20°$ C. and dried. Thereafter, 100 g of the defattened powder was suspended and stirred in 1 l of a 1M $NH_4SCN$ solution buffered with 0.02M Tris-HCl at pH 7.0-7.4. The suspension was separated into an extract and a precipitate by centrifugation. The precipitate was re-extracted with 1 l of the same solution. The extracts were combined to obtain a crude extract.

(2) DEAE-Sepharose chromatography:

The crude extract obtained by the above procedure (1) was diluted with the equal amount of a 0.02M Tris-HCl solution of pH 7.0-7.4, and then allowed to pass through a DEAE-Sepharose column equilibrated with a 0.02M Tris-HCl solution containing 0.02% of a non-ionic surfactant of Tween 80 and 0.25M $NH_4SCN$. The effluents were combined, to which NaCl was added to make the final concentration to be 1.0M. Its pH was adjusted at 7.4 with 1 N HCl.

Figure 1:
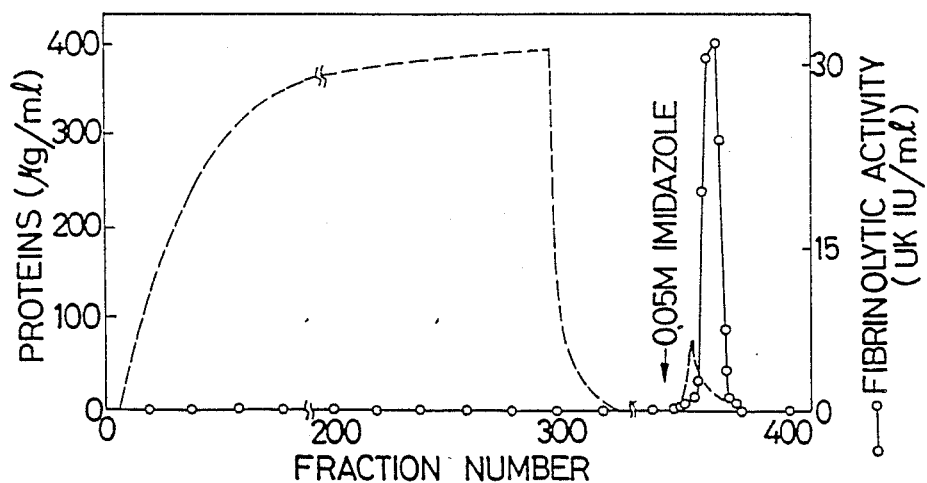
FIG. 1 is a zinc chelate-Sepharose chromatogram of the plasmingogen activator obtained in Example 1-(3)

(3) Zinc chelate-Sepharose chromatography:

The combined effluent obtained in the procedure (2) was passed through a zinc chelate-Sepharose column equilibrated with a 0.02M Tris-HCl solution of pH 7.0 containing 1.0M NaCl, 0.25M $NH_4SCN$ and 0.02M Tween 80. After washing with the equilibrating solution until the concentration of proteins in the eluate was lowered to less than 0.01 mg/ml, the column was washed further with a buffur solution the composition of which was identical to the equilibrating solution except that it contained no $NH_4SCN$ but 0.15M NaCl. The column was then washed with a 0.05M imidazole solution, thereby eluting the tissue activator into the washing agent. The profile of the resulting chromatogram is shown in FIG. 1.

Figure 2:
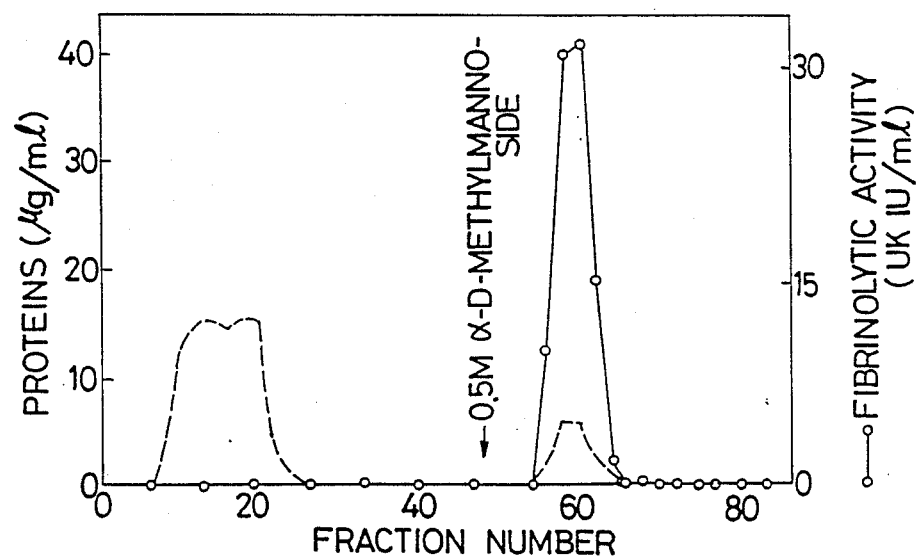
FIG. 2 is a concanavalin A-Sepharose chromatogram of the plasminogen activator obtained in Example 1-(4)

(4) Concanavalin A-Sepharose chromatography:

The tissue activator fractions obtained in the procedure (3) were passed through a concanavalin A-Sepharose column. The column had been equilibrated with a 0.02M Tris-HCl solution of pH 7.4 containing 0.15M NaCl and 0.02% Tween 80. After the column was washed with the equilibrating solution until the concentration of proteins in the eluate reached the base line, the tissue activator was eluted with an equilibrating solution containing 0.5M α-D-methylmannoside. The activator fractions were combined and the pH of the resultant solution was adjusted at 4.5 with acetic acid. The profile of the resultant chromatogram is shown in FIG. 2. Rijken et al. reported that a linear gradient eluent of α-D-methylmannoside (0–0.6M) is effective in the purification of a plasminogen activator isolated from human uterus tissue [Biochim Biophys. Acta. 580, 140-153 (1979)]. When the linear gradient eluent of α-D-methylmannoside (0–0.5M) was employed, the elution profile of the activator activity agreed with that of proteins. The elution points of almost all the plasminogen activators were near the elution point of the 0.35M α-D-methylmannoside solution and thus slightly higher than those reported by Rijken et al.

(5) CM-Sepharose chromatography:

The tissue activator fractions obtained in the procedure (4) were passed through a CM-Sepharose column. The column had been equilibrated with a 0.02M acetic acid buffer solution of pH 4.5 containing 0.15M NaCl and 0.02% Tween 80.

Figure 3:
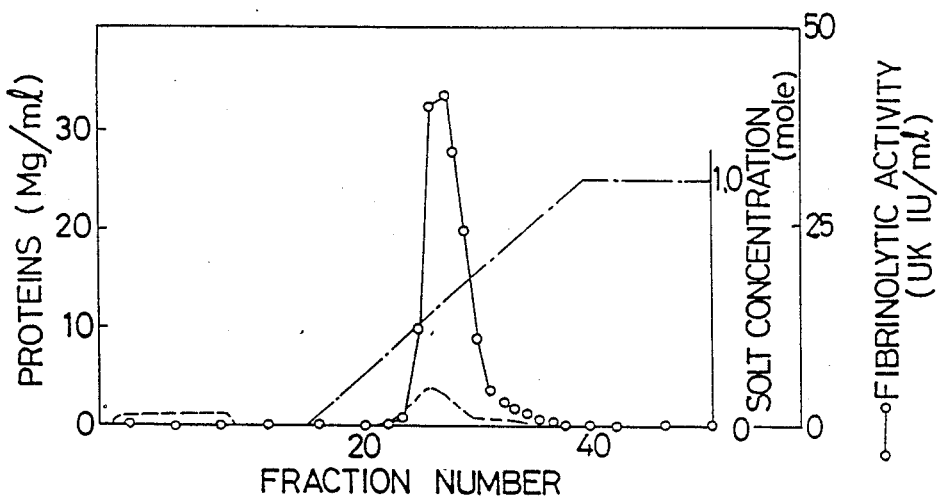
FIG. 3 is a CM-Sepharose chromatogram of the plasminogen activator obtained in Example 1-(5)

Washed first with the equilibrating solution, the column was developed with the same buffer solution except that the concentration of NaCl was linearly increased from 0.15M to 1.0M. The tissue activator was eluted near an NaCl concentration of 0.45M. The elution profile is illustrated in FIG. 3. The tissue activator was adsorbed onto the CM-Sepharose in the equilibrating solution and about 50–60% of the loaded proteins were passed through the column. The tissue activator was eluted near an NaCl concentration of 0.45M. This is equivalent to about 40% elution of the protein used. The specific activity was increased about 2.4 times. The activator fractions were collected and subjected to ultrafiltration through a Diaflo membrane PM10 (product of Amicon Corporation) to be concentrated. The exchange of buffer solution for the activator sample was effected on a Sephadex G-25 (product of Pharmacia AB) column. Having been equilibrated with a 0.02M Tris-HCl solution of pH 7.4 containing 1.0M NH$_4$SCN, the column was developed with the same buffer solution as the equilibrating solution. The thus-eluted protein fractions were combined together and subjected to ultrafiltration through a Diaflo membrane PM10 to be concentrated.

(6) Sephacryl S-200 gel filtration:

The concentrated sample of the tissue activator was passed through a Sephacryl S-200 (product of Pharmacia AB) column equilibrated with a 0.02M Tris-HCl solution of pH 7.4 containing 1.0M NH$_4$SCN.

Figure 4:
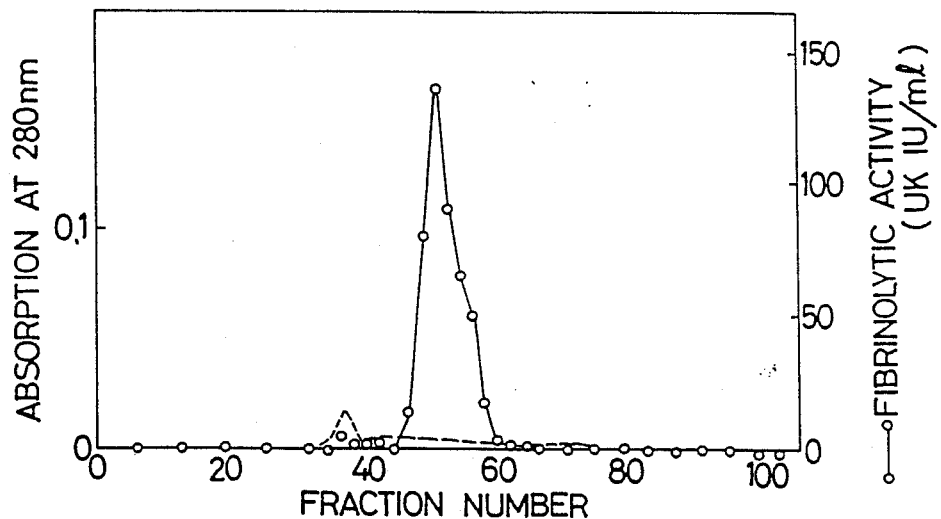
FIG. 4 is a diagram showing the results of Sephacryl S-200 gel filtration in Example 1-(6)
Figure 5:
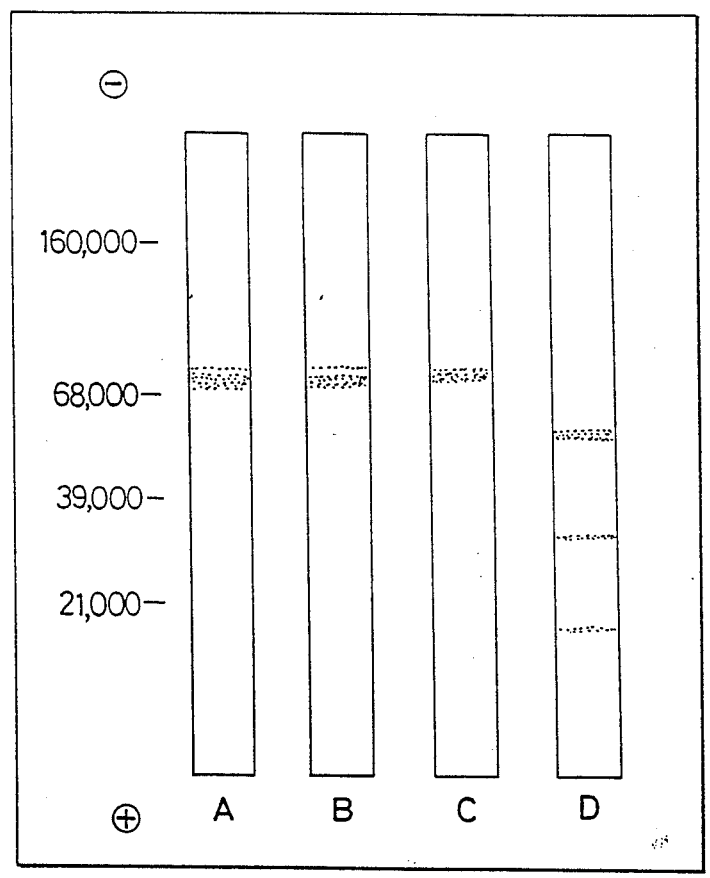
FIG. 5 is a diagram illustrating the SDS-polyacrylamide gel electrophoresis of the purified plasminogen activator isolated from kidneys according to the present invention. Letters A and B correspond to the purified activators extracted from kidneys and from vascular walls, respectively. Letter C corresponds to the activator secreted from cultivated normal human diploid and letter D corresponds to a commercially-available urokinase sample.

The effluents which were the fractions of the tissue activator were stored at −70° C. The elution profile is shown in FIG. 4.

EXAMPLE 2

Purification of plasminogen activator derived from blood vessel:

After a leg blood vessel was washed with a buffered physiological saline (pH 7.4), a plasminogen activator was extracted from the vascular walls with a 1M NH$_4$SCN solution. After the extract was salted out with a 50% ammonium sulfate solution, the resultant solution was subjected to arginine-Sepharose chromatography. The plasminogen activator showed strong affinity for the arginine-Sepharose and was eluted with a 0.5M arginine solution, whereby its specific activity was increased about 6 times.

Making use of the hydrophobic property of the plasminogen activator, the eluate was subjected to a phenyl-Sepharose chromatography. The adsorbed plasminogen activator was eluted with a 50% ethylene glycol solution or a 1% solution of a nonionic surfactant Triton X-100. The specific activity of the plasminogen activator was enhanced about 8 times in the above manner.

Most proteins were eluted in the earlier fractions of the effluent in the subsequent Sephacryl S-200 gel chromatography, while the plasminogen activator was eluted in the fractions corresponding to a molecular weight of about 70,000. At this stage, the specific activity was enhanced about 2.2 times.

Finally, the eluates containing the plasminogen activator were subjected to fibrin-Sepharose chromatography. The plasminogen activator derived from human blood vessel had strong affinity for the fibrin-Sepharose and the specific activity was thereby increased by 1.3 times.

The specific activity, purification, and percentage recovery at each of the stages carried out in the above manner are shown in Table 1.

TABLE 1

| Purification of Tissue Plasminogen Activator from Blood Vessels | | | | |
|---|---|---|---|---|
| Purification stage | Total activity (UKIU) | Specific activity (UKIU/mg) | Purification | Percentage recovery (%) |
| 1. Perfusate | 73,900 | 5.4 | 1 | 100 |
| 2. Extract salted out with ammonium sulfate | 75,400 | 400 | 74 | 102 |
| 3. Eluate through arginine-Sepharose | 72,400 | 2,300 | 426 | 96 |
| 4. Eluate through phenyl-Sepharose | 48,800 | 19,300 | 3,574 | 66 |
| 5. Eluate through Sephacryl S-200 | 31,000 | 42,000 | 7,796 | 42 |
| 6. Eluate through fibrin-Sepharose | 28,000 | 57,400 | 10,630 | 38 |

The specific activity of the final plasminogen activator was about 45,000–80,000 IU/mg proteins and the percentage recovery ranged from about 20% to 40%.

The molecular weight of the purified vascular plasminogen activator was about 70,000 as measured by the SDS polyacrylamide gel electrophoresis and its protein band was positive against the PAS dying, so that the plasminogen activator is basically believed to be a glycoprotein consisting of a single chain. The gel was sliced after the SDS-polyacrylamide gel electrophoresis to investigate the distribution of the activity of the plasminogen activator. As a result, it was found that the activity of the plasminogen activator was completely consistent with that of the protein band.

The isoelectric point (pI) of the main band of the vascular plasminogen activator according to the present invention was 7.8.

Using anti-urokinase IgG, the antigenicity of the plasminogen activator of the present invention was compared with that of urokinase. The activity of the vascular plasminogen activator was not inhibited at all by the anti-urokinase IgG and did not show any affinity for the anti-urokinase IgG-Sepharose.

An antivascular plasminogen activator obtained using the purified vascular plasminogen activator as an antigen inhibited the activity of the vascular plasminogen activator, but did not inhibit the activity of urokinase. Using the antivascular plasminogen activator and anti-urokinase serums, the antigenicities of the both activators were studied in accordance with the double immunodiffusion method. As a result, both urokinase and the vascular plasminogen activator developed individually a single precipitation curve between themselves and their corresponding anti-urokinase or antivascular plasminogen activator serum. However, no crosslinking was observed between the precipitation curves.

From the above results, it is understood that the vascular plasminogen activator according to the present invention is immunologically different from urokinase.

When the antivascular plasminogen activator IgG was added to a fibrin membrane in Todd's fibrinolysis autography, the activity of the plasminogen activator observed in vegetative blood vessels of inner and outer membranes of a vein was suppressed. As a result that the suppresion in activity of the vascular plasminogen activator was investigated using a variety of inhibitors, the activity inhibitions of 98% and 20% were observed respectively by diisopropyl fluorophosphate (5 mM) and L-arginine (0.1M), but no changes were observed by Trasylol (50 KIU/ml), iodoacetamide (10 mM) and soybean trypsin inhibitor (50 μg/ml). This indicates that the vascular plasminogen activator according to the present invention belongs, similarly to urokinase, to serine protease.

EXAMPLE 3

Analysis of tissue plasminogen activator and its results:

(1) Unless otherwise specifically indicated, the plasminogen activator was analyzed by the fibrinagar plate method disclosed in Immunochemistry 9, 709–723 (1972). The fibrinolytic activity of the tissue activator was compared with that of urokinase and was expressed in terms of the international unit (UKIU). The standard curves showing the activity of serial dilutions of both the plasminogen activator of the present invention and urokinase were straight in the range of the lytic area of 70–240 mm² proportional to the dilution degree of each enzyme. However, the gradient of the standard curve of the tissue activator was not completely consistent with that of urokinase. The activity of the tissue activator was determined by measuring the lytic areas of diluted samples within the range of 120–200 mm². The lytic area of 10 μl of a 1 IU/ml urokinase solution was 156 mm². The reproducibility of the fibrin-agar plate method was ±6%. The enzymatic activity of the tissue activator was standardized by the enzymatic activity of urokinase and the percentage recovery of the tissue activator and its specific activity relative to UKIU/ml were measured after each of several purification stages.

The non-specific fibrin-resolving activity was measured on a fibrin-agar plate free of plasminogen.

In some cases, the measurement was made in accordance with a method using $^{125}$I-fibrin monomer trapped in a cellulose nitrate disc ("Selectgun" Type-BA; pore diameter, 0.2 μm) [Progress in Chemical Fibrinolysis and Thrombolysis, Vol. 3, 539–546 (1978), Raven Press, New York]. Fibrinogen free of human plasminogen was radiated by the method proposed by Hawker et al. [J. Clin, Pathol. 29, 495–501 (1976)]. The specific activity of the labeled substrate was 0.018 mci/mg fibrinogen. A sample mixture was incubated at 37° C. and each 50 μl portion was sampled after 1 hour and 7 hours, released $^{125}$I from which portion was measured by an automatic gamma counter. The activity of each of the diluted solutions of the tissue activator and urokinase was expressed in terms of the percentage of the released $^{125}$I relative to the total radioactivity by subtracting the released $^{125}$I.

(2) Affinity chromatography on anti-urokinase IgG-Sepharose column:

The urokinase antiserum was obtained from a goat immunized by a subcutaneous administration of 1 mg of high-purity human urokinase (M.W., 33,000; specific activity, 202,400 IU/mg). The employed urokinase sample was identical to that analyzed in accordance with the SDS-polyacrylamide gel electrophoresis.

The urokinase antiserum showed only one precipitation curve for urokinase antigen when examined in accordance with the double immunodiffusion analysis. IgG fractions of anti-urokinase goat serum and unimmunized goat serum were prepared by precipitating with a saturated 33% ammonium sulfate solution and purified further by DEAE-Sepharose chromatography.

The anti-urokinase IgG (50 μg/ml) added to a fibrin plate inhibited completely the activity of the commercial urokinase sample used as an antigen (5,000 IU/ml).

These IgG samples (20 mg/ml) individually developed a single precipitation curve when the immunoelectrophoresis was applied using anti-goat serum rabbit serum.

Figure 7:
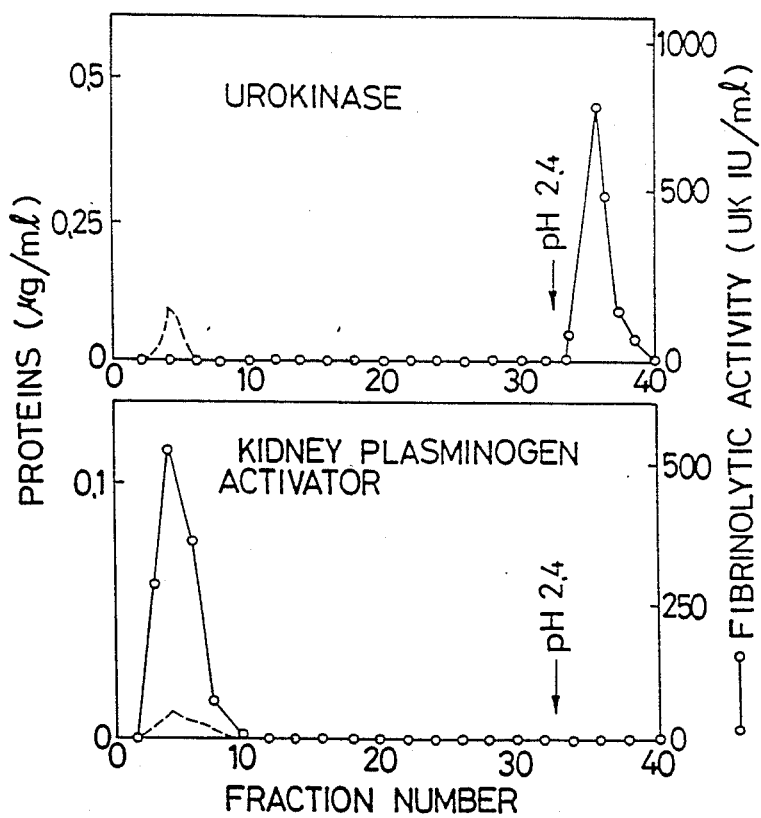
FIG. 7 is a diagram showing affinity chromatograms of urokinase and the kidney-originated plasminogen activator of the present invention, both obtained by using anti-urokinase IgG-Sepharose columns.

50 mg of the anti-urokinase or normal IgG sample was coupled with 15 ml of cyanogen bromide-activated Sepharose CL-4B in accordance with the method proposed by Cuatrecasas [J. Biol. Chem. 245, 3059–3065, (1970)]. The gel was washed with a 0.02M Tris-HCl solution of pH 7.4 containing 1.0M NaCl at least 20 times in volume that of the gel. The chromatograms of the tissue activator and urokinase are shown in FIG. 7.

(3) Adsorption of the tissue activator and urokinase onto fibrin-Sepharose:

In accordance with the above Cuatrecasas's method, 200 mg of fibrinogen free of human plasminogen was coupled at pH 8.3 with 20 mg of cyanogen bromide-activated Sepharose CL4B. The coupled fibrinogen was then activated by the addition of thrombin (1 Unit/ml) according to the method proposed by Heeme et al. 20 [Thromb. Res. 2, 137–143 (1973)]and thereafter washed with a 0.02M Tris-HCl solution of pH 7.4 containing 0.15M NaCl, 0.1% Triton X-100 and 1 μM Aprotinin (product of Beyer AG). The gel loaded in the column was washed with 2M NH₄SCN dissolved in a buffer solution and then with the buffer solution in volume 10 times that of the gel. A sample of urokinase or the tissue activator (obtained in the procedure (6) of Example 1) in the buffer solution was added to the column. After washing, the column was eluted with a 2M NH₄SCN solution. The activity of the plasminogen activator was measured by the method utilizing the protein concentration in the eluate and a chromogenic substrate-S-2288.

(4) Other methods:

The quantitative analyses of proteins were conducted in accordance with the method proposed by Lowry et al. [J. Biol. Chem. 193, 265–275 (1951)]using bovine serum albumine as a standard protein. Solubilized proteins in Tween 80 were quantitatively analyzed by the method proposed by Shiu et al. [J. Biol. Chem. 249, 7902–7911 (1974)], after the sediment was removed by centrifugation. In some cases, a more accurate method making use of fluorescamine was applied [Arch. Biochem. Biophys. 155, 213–220 (1973)]. The eluates obtained after the Sephacryl S-200 chromatography were monitored using an LKB Uviicord II detector and recorder equipped with a Hitachi Spectrophotometer Model 200-200.

The SDS-polyacrylamide gel electrophoresis was conducted in accordance with the method proposed by Weber et al. [J. Biol. Chem. 244, 4406–4412 (1972)]. Each protein sample was incubated at room temperature for 30 minutes in a 1.0% SDS solution and subjected to electrophoresis in a 5% polyacrylamide gel. In some instances, proteins were reduced with a 1% solution of 2-mercaptoethanol. The gel was dyed in protein with Coomassie Brilliant Blue or in glycoprotein with periodic acid-Shiff's reagent. In order to measure the activity of the plasminogen activator, the SDS polyacrylamide gel electrophoresis was conducted in a 5% polyacrylamide gel in accordance with the slab gel system. After the electrophoresis, the slab gel was washed at room temperature for 2 hours with a 0.01M phosphoric acid buffer solution of pH 7.4 containing 0.5M NaCl and 2% Tween 80. The gel was then stacked with a 1% agarose gel containing 0.2% human fibrinogen (either rich in or free of plasminogen) and 0.5 unit of thrombine. The contents were then incubated for 1–7 hours at 37° C. in a constant-humidity chamber and the agarose and polyacrylamide gels were dyed with Coomassie Brilliant Blue. The molecular weight of the protein was measured by comparing its mobility with that of the standard protein in accordance with the aforementioned method proposed by Weber et al.

The measurement of the isoelectric point of the purified tissue activator was carried out in a 7.5% polyacrylamide gel containing 8M urea and 1% ampholite in accordance with the method proposed by Mertz et al. [Biochem. Biophys. Res. Commun. 49, 84–91 (1972)]. The sample was solubilized in an 8M urea solution containing 2 mM EDTA and 1% ampholite. Its pH was determined by the method proposed by Finlayson et al. [Anal. Biochem. 40, 292–311 (1971)].

The thus-purified tissue activator was tested with various fluorescent substrates by adding 50 μl of the tissue activator sample in a 0.02M Tris-HCl solution of pH 8.0 containing 0.1M NaCl and 0.02% Tween 80 and 2.0 ml of the substrate in the same buffer solution. The following materials were used as the fluorescent substrates:

Boc-L-valyl-L-prolyl-L-arginine-4-methyl-coumaryl-7-amide;
Carbobenzoxy-L-phenylalanyl-L-arginine 4-methyl-coumaryl-7-amide;
L-prolyl-L-phenylalanyl-L-arginine-4-methylcoumaryl-7-amide; and
Glutaryl-glycyl-L-arginine-4-methylcoumaryl-7-amide.

The initial release of 7-amino-4-methylcoumarine (AMC) was measured by a fluorometer at 37° C. in a Shimadzu Fluorospectrophotometer Model RF-520. The fluorometer had been set in such a manner that a radiation of a fluorescent light of 380 nm permitted to emit an excited fluorescent light of 460 nm, and also so adjusted that a 0.1% DMSO solution containing 0.2M AMC gave a relative fluorescent unit of 1.0. The hydrolytic activity of the purified tissue activator was measured using a chromogenic substrate, by adding 200 μl of a tissue activator sample, 200 μl of a 0.1M Tris-HCl solution of pH 8.0 containing 0.1M NaCl and 0.02% Tween 80, and 200 μl of a 3 mM S-2251 solution or a 1 mM S-2288 solution. The initial release of p-nitroaniline was measured by a spectrophotometer at 405 nm and 37° C. in a glass cell. The initial velocity of the hydrolytic activity was expressed in terms of ΔmA/min for the chromogenic substrate and Δ%/min for the fluorescent substrate.

The inhibitory effects of the tissue activator when treated respectively with diisopropyl fluorophosphate, iodoacetamide, soybean trypsin inhibitor and L-arginine aprotinin were tested with the chromogenic substrate S-2288. The purified tissue activator samples were incubated at 37° C. for 1 hour after the addition of the inhibitor thereto. To a 200 μl portion taken out from each mixture were added 200 μl of the buffer solution and 1 mM of the substrate. By comparing the value ΔA/min, the inhibitory effect of each reagent was measured.

(5) The samples were purified by the method of Example 1 and analyzed in accordance with the analytical method described in Example 2. Results are shown in Table 2.

TABLE 2

Purification of Tissue Plasminogen Activator Obtained from Kidneys

| Purification stage | Total activity (UKIU) | Specific activity (UKIU/mg) | Purification | Percentage recovery (%) |
|---|---|---|---|---|
| 1. NH4SCN extract | 8,600 | 0.8 | 1 | 100 |
| 2. Eluate through DEAE-Sepharose | 7,800 | 2.0 | 2.4 | 90 |
| 3. Eluate through arginine-Sepharose | 6,200 | 300 | 357 | 72 |
| 4. Eluate through concanavlin A-Sepharose | 4,300 | 5,280 | 6,286 | 50 |
| 5. Eluate through CM-Sepharose | 3,500 | 12,300 | 14,600 | 41 |
| 6. Eluate through Sephacryl S-200 | 2,700 | 25,700 | 30,600 | 31 |

EXAMPLE 4

Figure 6:
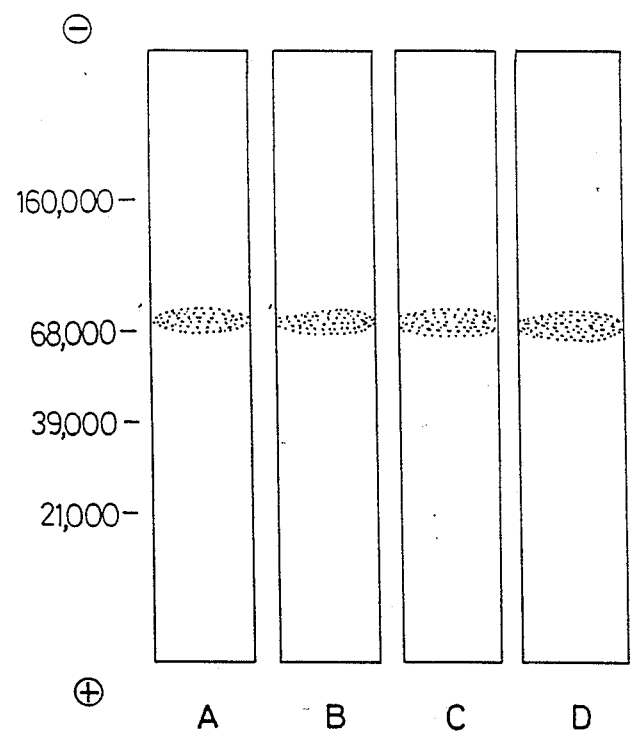
FIG. 6 is a diagram showing the identification of the plasminogen activators of the present invention subjected in advance to SDS-polyacrylamide gel electrophoresis. Letters A and B correspond to the purified plasminogen activators obtained in Example 1-(6), while letters C and D are the crude extracts obtained in Example 1-(3). A polyacrylamide gel was used to obtain the activators A and C, whereas a fibrin-agarose gel was used for obtaining the activators B and D.

Properties of the tissue plasminogen activator of the present invention:

(1) Molecular weight:

The molecular weight of the purified tissue activator obtained in Example 1-(6) was measured by the SDS-polyacrylamide gel electrophoresis, with the result that the molecular weight of the kidney-originated activator and that of the vascular activator were about 72,000 and 70,000, respectively. These tissue activators were positive to the periodic acid-Schiff's reagent, thereby indicating the presence of sugar chains. In the case of the kidney-originated activator, for instance, the mobility of the principal band of the purified tissue activator as measured by the electrophoresis was identical to the mobility of the principal band of resolved fibrin of a crude extract, when the crude extract and purified tissue activator were respectively analyzed by the SDS-polyacrylamide gel electrophoresis and the resulting gels were respectively developed on fibrin-agar plates. This indicates that the molecular weight was 70,000 (see, FIG. 6). The band of resolved fibrin was attributed to the presence of plasminogen in the fibrin-agar plate.

From the above finding, it is understood that the crude extract obtained from human kidney tissue contains a plasminogen activator and the plasminogen activator consists principally of that having an apparent molecular weight of about 70,000. A similar experiment conducted using an activator derived from a blood vessel gave an estimated molecular weight of about 70,000 for the activator.

(2) Isoelectric points:

As the isoelectric points of the purified activators, the main peaks appeared at 8.2 in the case of a kidney-originated activator and at 7.8 for an activator derived from a blood vessel. After measurement of each isoelectric point, the activity of the activators was measured on a fibrin-agar plate which was in the form of a thin-film gel (thickness: 1.5 mm). Their activities were found respectively near their isoelectric points, i.e., pH 8.2 and 7.8.

(3) Immunological differences between tissue activators and urokinase:

In order to study whether the activators obtained respectively from kidney tissue and the wall of a blood vessel have the same antigenicity as urokinase, the elution profile of proteins and active ingredient of the activator obtained by the antiurokinase IgG-Sepharose affinity chromatographic treatment of the purified activator of Example 1-(6) and the activator of Example 1-(3) was compared with the elution profile of urokinase. Results are shown in FIG. 7. As seen from FIG. 7, urokinase was adsorbed strongly onto the column and almost all the loaded activity was eluted with a 0.1M glycine-HCl solution of pH 2.4 containing 0.15M NaCl and 0.1% Triton X-100. The protein contained in the effluents was serum albumine incorporated in the commercially available urokinase used in this experiment. On the other hand, the purified activator was passed through the column without adsorption, and neither protein nor activity was eluted with the glycine solution of pH 2.4. When the partially-purified sample obtained in Example 1-(3) was poured in the same column, about 15% of the poured activity was adsorbed on the column and eluted with the glycine solution of pH 2.4. On the basis of these findings, it is envisaged that the plasminogen activator of the present invention is a tissue activator which is immunologically dissimilar to urokinase and the crude extract obtained from kidneys contains urokinase or an urokinase-like activator as a minor ingredient. On the other hand, the antiserum for the vascular wall activator underwent a ready crosslinking reaction with the activator derived from kidneys, thereby indicating that the both activators are similar to each other also from immunological viewpoint.

(4) Affinity of tissue activators for fibrin-Sepharose:

The affinity of each of urokinase and the tissue activator for insolubilized fibrin monomer was investigated using fibrin-Sepharose columns.

The tissue activator according to the present invention [Example 1-(6)] was adsorbed completely onto the fibrin-Sepharose column. It was then eluted with a 2M NH$_4$SCN solution and at least 90% of the total poured activity was recovered. On the other hand, almost all the active ingredients of urokinase were passed through the column, so that the activity of the activator was not found in the eluate obtained with a 2M NH$_4$SCN solution from the column. As has been mentioned above, the tissue activator obtained from human kidney according to the present invention has a strong affinity for fibrin-Sepharose.

(5) Specificity of synthetic substrates to tissue activators:

The specificity of certain synthetic substrates to the activator obtained in Example 1-(6) was studied. The following substrates were employed.

For plasmin, H-D-valyl-L-leucyl-L-lysine-p-nitroanilide dihydrochloride (S-2251);

For natural thrombin, Boc-L-valyl-L-prolyl-L-arginine-4-methylcoumaryl-7-amide (3093-V);

For plasma, carbobenzoxy-L-phenylalanyl-L-arginine-4-methylcoumaryl-7-amide (3095-V);

For urine kallikrein, L-prolyl-L-phenylalanyl-L-arginine-4-methylcoumaryl-7-amide (3096-V);

For urokinase, glutamyl-glycyl-L-arginine 4-methylcoumaryl-7-amide (3097-V); and For tissue plasminogen activator, H-D-isoleucyl-L-prolyl-L-arginine-p-nitroanilide dihydrochloride (S-2288).

The tissue activator of the present invention did not show hydrolytic activity to any substrates other than S-2251 and S-2288. The activity (100 UKIU/ml) of the tissue activator according to the present invention was 88 ΔmA/min against S-2251 and 70 ΔmA/min against S-2288.

The activator of the present invention showed some characteristic properties when treated with certain inhibitors. The amide-decomposing activity of the activator of the present invention against S-2288 was not inhibited where 50 KIU/ml of Aprotinin, 10 mM of iodoacetamide or 50 mg/ml of soybean trypsin was used as an inhibitor, but it was inhibited upto 26% by 100 mM of L-arginine and upto 98% by 5 mM of diisopropyl fluorophosphate.

(6) Stability:

The plasminogen activator according to the present invention did not give any activity reduction even after storing at 4° C. in a buffer solution of pH 7.4 for 2 weeks. The same result was obtained even when 1M NH$_4$SCN or 0.02% Tween 80 and 0.1M NaCl were incorporated in the buffer solution.

The stability of the plasminogen activator of the present invention was investigated in the pH hours in a buffer solution range of 1–10 at 4° C. for 24 containing 0.5M NaCl and 0.02% Tween 80. As a result, it was found that the plasminogen activator of the present invention was stable within the pH range of 2–10, but the activity was reduced by 70% at pH 1.0.

As has been described in detail, the activator of the present invention is a novel plasminogen activator different from urokinase and plays an important role in the control of the recovery of a tissue including the decomposition of fibrin deposits on inner and outer vascular walls at a damaged part.

Needless to say, the novel plasminogen activator according to the present invention can be isolated from various organs of mammalian animals. Accordingly, any plasminogen activators must be assumed to fall within the scope of the present invention irrespective of their origins, so long as they have properties characteristic to the plasminogen activator of the present invention.

By way of the preparation process of the activator according to the present invention, the tissue activator can be isolated in a highly purified form so that the activator may have a specific activity as large as 30,000–45,000 times the specific activity of a human kidney dried with acetone.

I claim:

1. A process for preparing a plasminogen activator having the following characteristic properties:
   (1) a main protein band obtained by sodium dodecyl sulfate-polyacrylamide gel electrophoresis having a molecular weight of approximately 70,000 ±5,000;
   (2) a main band obtained by isoelectric-point electrophoresis having a pI in the range of 7 to 9;
   (3) an immunological property of not being adsorbed by antiurokinase IgG-agarose affinity chromatography; and
   (4) a property wherein plasminogen activator hydrolyzes H-D-valyl-L-leucyl-L-lysine-p-nitroanilide dihydrochloride and H-D-isoleucyl-L-prolyl-L-arginine-p-nitroanilide dihydrochloride, but does not hydrolyze Boc-L-valyl-L-prolyl-L-arginine-4-methylcoumaryl-7-amide, carbobenzoxyl-L-phenylalanyl-L-arginine-4-methylcoumaryl-7-amide, 1-prolyl-L-phenylalanyl-L-arginine-4-methylcoumaryl-7-amide and glutaryl-glycyl-L-arginine-4-methylcoumaryl-7-amide, which process comprises:

(i) subjecting a human blood vessel or kidney to an extraction treatment with an ammonium thiocyanate solution;

(ii) salting the extract out with an $(NH_4)_2SO$ solution, passing the resulting solution through an arginine agarose column, and then washing the column with an arginine solution to elute the adsorbed plasminogen activator thereunto;

(iii) passing the fraction of the eluted plasminogen activator in step (ii) through a phenyl-agarose column and washing the column with an ethylene glycol solution or a nonionic surfactant solution to elute the adsorbed plasminogen activator thereunto;

(iv) passing the fraction of the eluted plasminogen activator in step (iii) through a dextran gel column then through a fibrin-agarose column;

(v) eluting with a $NH_4SCN$ solution; and (vi) then recovering the plasminogen activator in the solution.

* * * * *